United States Patent
Corrin et al.

(10) Patent No.: US 10,611,950 B2
(45) Date of Patent: Apr. 7, 2020

(54) COMPOSITION AND METHOD FOR CONTROLLING BACTERIA IN FORMATIONS

(71) Applicant: BIOTECHNOLOGY SOLUTIONS, LLC, Houston, TX (US)

(72) Inventors: Edward Corrin, Houston, TX (US); Michael Gurecki, Houston, TX (US); Michael Harless, Houston, TX (US)

(73) Assignee: BIOTECHNOLOGY SOLUTIONS, LLC, Houston, TX (US)

( * ) Notice: Subject to any disclaimer, the term of this patent is extended or adjusted under 35 U.S.C. 154(b) by 0 days.

(21) Appl. No.: 16/029,963

(22) Filed: Jul. 9, 2018

(65) Prior Publication Data

US 2019/0010379 A1  Jan. 10, 2019

Related U.S. Application Data

(60) Provisional application No. 62/530,678, filed on Jul. 10, 2017.

(51) Int. Cl.
*C09K 8/532* (2006.01)
*E21B 43/26* (2006.01)
*C09K 8/582* (2006.01)

(52) U.S. Cl.
CPC .............. *C09K 8/532* (2013.01); *C09K 8/582* (2013.01); *E21B 43/26* (2013.01); *C09K 2208/20* (2013.01)

(58) Field of Classification Search
None
See application file for complete search history.

(56) References Cited

U.S. PATENT DOCUMENTS

| | | | |
|---|---|---|---|
| 5,405,531 A * | 4/1995 | Hitzman | A01N 59/00 166/307 |
| 2009/0223892 A1 * | 9/2009 | Vollmuth | A61L 9/01 210/631 |
| 2012/0067566 A1 * | 3/2012 | Durham | C09K 8/68 166/246 |

* cited by examiner

*Primary Examiner* — Andrew Sue-Ako
(74) *Attorney, Agent, or Firm* — Adolph Locklar

(57) ABSTRACT

A process includes growing NRB in a nitrate reducing bacteria media to form a NRB culture and combining the NRB culture with a concentrated nitrate solution to form a NRB composition.

10 Claims, No Drawings

COMPOSITION AND METHOD FOR CONTROLLING BACTERIA IN FORMATIONS

CROSS-REFERENCE TO RELATED APPLICATIONS

This application is a non-provisional application which claims priority from U.S. provisional application No. 62/530,678, filed Jul. 10, 2017, which is incorporated by reference herein in its entirety.

FIELD OF THE DISCLOSURE

Embodiments of the present disclosure generally relate to controlling and reducing bacteria, such as sulfate-reducing bacteria (SRB) in hydrocarbon-bearing formations.

BACKGROUND

Water in hydrocarbon formations may provide a growth media for anaerobic bacteria. Certain anaerobic bacteria, such as SRB, may be problematic in recovery of hydrocarbons from hydrocarbon-bearing formations. For instance, SRB may reduce sulfates to sulfides, which may damage the hydrocarbon-bearing formation. In addition, SRB may form slimes or sludges, reducing the porosity of the formation. Reducing the porosity of the formation may impede recovery of the hydrocarbons from the hydrocarbon-bearing formation. Reduction of porosity may be a particularly acute problem in low porosity formations, such as shale.

Fracturing operations may be used to increase hydrocarbon recovery from hydrocarbon-bearing formations. Fracturing operations make use of fracturing fluids, which are often water-based. Depending on the formation and the fracturing operation method, water-based fracturing fluid may be retained in the formation for extended periods. For instance, small-pore sized, low-porosity shales may retain a significant amount of water-based fracturing fluid. The water retained in the formation from the fracturing operation may provide a growth media for SRB.

Traditional water-based fracturing fluids may include a biocide to control SRB. However, biocides, in particular long-acting biocides such as glutaraldehyde, may present environmental concerns, such as ground water contamination. Short acting biocides, such as oxidizers, may present less of an environmental hazard, but may not be active over the entire time period in which the fracturing fluid is retained by the hydrocarbon-bearing formation.

Nitrate-Reducing Bacteria (NRB) may inhibit the growth of SRB by using a more efficient nitrate-reduction metabolic pathway than SRB and removing nutrients from the environment that SRB require in order to grow and produce sulfides. Traditionally, NRB require a high concentration of nitrate in water in the hydrocarbon to be effective and, thereby necessitating large quantities of nitrate to be pumped simultaneously with the NRB into the hydrocarbon-bearing formation.

SUMMARY

The present disclosure provides for a process that includes growing NRB in a nitrate reducing bacteria media to form a NRB culture and combining the NRB culture with a concentrated nitrate solution to form a NRB composition.

The present disclosure also provides for a NRB composition that includes NRB, water, and nitrate, the nitrate present in the NRB composition in a concentration of between 10% and 50% active nitrate.

The present disclosure also provides for a process that includes growing nitrate reducing bacteria (NRB) in a nitrate reducing bacteria media to form a NRB culture and combining the NRB culture with molybdate or molybdate salt to form a NRB composition.

DETAILED DESCRIPTION

A detailed description will now be provided. The following disclosure includes specific embodiments, versions and examples, but the disclosure is not limited to these embodiments, versions or examples, which are included to enable a person having ordinary skill in the art to make and use the disclosure when the information in this application is combined with available information and technology.

Various terms as used herein are shown below. To the extent a term used in a claim is not defined below, it should be given the broadest definition persons in the pertinent art have given that term as reflected in printed publications and issued patents. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.).

Certain embodiments of the present disclosure relate to a NRB composition that includes a nitrate and NRB with a nitrate concentration that is effective in controlling SRB while retaining NRB viability. In certain embodiments, the composition is a solution.

The NRB may be, for example and without limitation, *Campylobacter* sp. *Nitrobacter* sp., *Thiobacillus* sp., *Nitrosomonas* sp., *Thiomicrospira* sp., *Sulfurospirillum* sp., *Thauera* sp., *Paracoccus* sp., *Pseudomonas* sp., or *Rhodobacter* sp., Specific examples of NRB include, but are not limited to, *Nitrobacter vulgaris, Nitrosomonas europea, Pseudomonas stutzeri, Pseudomonas aeruginosa, Paracoccus denitrificans, Sulfurospirillum deleyianum*, and *Rhodobacter sphaeroides.*

Nitrates included in the NRB composition may be for instance, sodium nitrate, calcium nitrate, potassium nitrate, silver nitrate, or a combination thereof. In certain embodiments, only sodium nitrate is used in the NRB composition. Without being bound by theory, sodium nitrate may allow greater survivability of the NRB than other nitrates. Further, sodium nitrate may be sufficiently soluble in water as to be efficacious in providing nutrients to the NRB of the NRB composition.

In certain embodiments, the amount of active nitrate in the NRB composition may range from 0.5% to 50%, or from 20% to 40% or about 30% (weight of active nitrate to volume of NRB composition). In some embodiments, the amount of NRB culture may range from 5% to 50%, from 10 to 40% or about 30% (volume/volume). The remainder of the NRB composition may be water.

The NRB composition may be prepared by growing NRB in a nitrate reducing bacteria media composed of potassium monophosphate, yeast, sodium nitrate, sodium acetate, sodium lactate, sodium chloride, or other suitable constituents for growth of NRB. The resulting NRB culture may be combined with a concentrated nitrate solution. For example, when the nitrate is sodium nitrate, the concentrated sodium nitrate solution may be between 40 and 70% sodium nitrate, between 50 and 60% sodium nitrate, or about 59% sodium nitrate. In embodiments, nitrate concentration is selected in part at a level below which the nitrate precipitates out of the concentrated nitrate solution.

In some embodiments, the shelf life of the NRB composition is between 30 days and 18 months or between 6 months and 12 months, or at least 30 days. Shelf life refers to time NRB in an NRB composition may remain capable of reproducing when exposed to suitable conditions, such as, temperature, salt concentration, appropriate nutrients, and other environmental factors.

In certain embodiments, the NRB composition may be introduced into a hydrocarbon-producing formation, such as by pumping. In some embodiments, the NRB composition may be introduced into the formation together with a fracturing fluid.

In certain embodiments, SRB inhibitors, such as molybdates and molybdate salts may be used in conjunction with the NRB composition or injected separately. For instance, molybdates may be introduced together with the NRB composition into the formation, such as with a fracturing fluid or at a different time. The molybdates and molybdate salts may include sodium molybdate and lithium molybdate, although any SRB inhibitor may be used. In certain embodiments of the present invention, molybdates and molybdate salts are added to the fracturing fluid in the range of 5 to about 100 ppm, or between 10 and 80 ppm by weight of fluid. In other embodiments, the molybdate and molybdate salts are included in the NRB composition in an amount from 1.5% to 25%, or from 3% to 15% of the NRB composition (by weight of fluid).

In yet other embodiments, the nitrate may be omitted and the NRB composition may include the molybdate/molybdate salt and the NRB. In such embodiments, the molybdate and molybdate salts are included in the NRB composition in an amount from 1.5% to 25%, or from 3% to 15% of the NRB composition (by weight of fluid).

EXAMPLES

The disclosure having been generally described, the following examples show particular embodiments of the disclosure. It is understood that the example is given by way of illustration and is not intended to limit the specification or the claims.

Example 1

A NRB composition was prepared by growing NRB in nitrate reducing bacteria media, then mixing with concentrated sodium nitrate ($NaNO_3$) solution @58.75% in a ratio of 30% NRB culture to 70% concentrated $NaNO_3$. The final NRB composition was 30% live culture NRB at 30% active nitrate (42.9% $NaNO_3$).

Example 2

NRB compositions were prepared as in Example 1, with the exception of the control, but with different concentrations of sodium nitrate as shown in Table I. The control had no nitrate solution and used deionized water. Bottles of the NRB composition were made for each concentration and allowed to sit covered at ambient temperature (25° C.). At each time specified, a sample of the NRB solution was withdrawn and used to perform a serial dilution into nitrate reducing bacteria media which was then grown at the NRB's optimal temperature of 45° C. The serial dilution procedure used for this work followed The American Petroleum Institute's Recommended Practice 38 (API RP38). Using this procedure, each vial in the series represents a one log increase in viable bacteria (e.g 5 positive vials represents $10^5$ or 100,000 bacteria in the original sample). The dilutions were carried out to the 8th vial (representing $10^8$ bacteria in the original sample) and growth and successful reduction of nitrate were checked.

TABLE 1

| | Log Survival | | | | |
| --- | --- | --- | --- | --- | --- |
| Percent Nitrate (w/v) | 0 months | 3 months | 6 months | 9 months | 12 months |
| Control | 8 | 8 | 8 | 8 | 8 |
| 10% Active NO3 | 8 | 8 | 8 | 8 | 6 |
| 20% Active NO3 | 8 | 8 | 8 | 6 | 5 |
| 30% Active NO3 | 8 | 8 | 8 | 5 | 5 |
| 40% Active NO3 | 8 | 3 | 0 | 0 | 0 |
| 50% Active NO3 | 8 | 0 | 0 | 0 | 0 |

The control showed no signs of decreased viability over the course of the experiment while concentrations above 30% active nitrate began to kill the NRB within the first 3 months. 30% and 20% active nitrate solutions did not begin to have an effect on NRB survival until 9 months, and the 10% active nitrate solution only began to impact NRB survival beyond 9 months. While 50% and 40% active nitrate proved fatal to the NRB within half a year, the reduction in survival from 30% and below was relatively mild and 10,000 cells/mL or more live NRB were present in those solutions even after a full year.

Example 3

NRB compositions were prepared as in Example 1, but with different types of nitrates. Bottles of the NRB composition were made for each type of nitrate and allowed to sit covered at ambient temperature (25° C.). At each time specified, a sample of the NRB solution was withdrawn and used to perform a serial dilution into nitrate reducing bacteria media which was then grown at the NRB's optimal temperature of 45° C. The dilutions were carried out to the 8th vial and growth and successful reduction of nitrate were checked. Results are shown in Table 2.

TABLE 2

| | Log Survival | | | |
| --- | --- | --- | --- | --- |
| Nitrate Type and % | Time 0 | 1 week | 2 weeks | 4 weeks |
| 30% via NaNO3 | 8 | 8 | 8 | 8 |
| 30% via Ca(NO3)2 | 8 | 0 | 0 | 0 |
| 20% via KNO3 | 8 | 8 | 8 | 8 |
| 0.1% via AgNO3 | 8 | 0 | 0 | 0 |

When using calcium nitrate ($Ca(NO_3)_2$) the NRB were dead in only a week. Potassium nitrate ($KNO_3$) did not have an acute negative effect on NRB survival compared with sodium nitrate, however due to solubility, $KNO_3$ cannot be used at 30% active nitrate because of salting out of solution. As a result, potassium nitrate was tested at only 20% active nitrate. Silver nitrate ($AgNO_3$) suffers from even more pronounced solubility issues and has strong antimicrobial properties that further complicate usage as a nitrate source for NRB. Tested at a concentration of just 0.1% active nitrate, silver nitrate killed all of the NRB in under a week.

Example 4

Hydrogen sulfide inhibition was tested in mock-produced water approximating water used in hydraulic fracturing operations and was made to a total dissolved solids concentration of 3% with a mixture of instant ocean and NaCl salts. The water was supplemented with nutrients and sulfate to allow SRB to metabolize and create $H_2S$. The water was spiked with SRB and then treated with the various treatment conditions noted below in Table 3 and sealed. Treatment conditions were:
Control: No biocide or nitrate.
250 ppm 12:3 Glut/Quat Biocide: a mixture of glutaraldehyde and a quarternary ammonia compound was prepared
NRB Program: (480 ppm $Ca(NO_3)_2$ with 1 ppm live NRB culture.
240, 260, and 300 ppm NRB composition—NRB concentration at 30% active nitrate and 30% NRB culture.

$H_2S$ was measured at intervals using $H_2S$ detecting Draeger tubes. Dissolved $H_2S$ was released into the gas phase with the addition of hydrochloric acid so that $H_2S$ could be measured with the Draeger tubes to get a complete reading of all $H_2S$ produced during the course of the example.

TABLE 3

| Treatment | H2S Gas (ppm) |
| --- | --- |
| Control | 3000 |
| 250 ppm 12:3 Glut/Quat Biocide | 6 |
| NRB Program (480 ppm CaNO3) | 40 |
| 240 ppm NRB Composition | 120 |
| 260 ppm NRB Composition | 160 |
| 300 ppm NRB Composition | 0 |

The NRB composition at 300 ppm was able to completely control $H_2S$ outperforming the normal NRB program and performing at least as well as traditional Glut/Quat biocide. At 260 ppm and 240 ppm, the NRB composition resulted in a significant reduction in the amount of $H_2S$ produced compared to control, performing similarly to the normal NRB program.

Example 5

Samples were prepared in accordance with Example 4, except that actual produced water sourced from the Eagle Ford shale that was diluted to 3% using deionized water was used in the samples. Results are shown in Table 4.

TABLE 4

| Treatment | H2S Gas (ppm) |
| --- | --- |
| Control | 3000 |
| 250 ppm 12:3 Glut/Quat Biocide | 6 |
| NRB Program (480 ppm CaNO3) | 40 |
| 240 ppm NRB Composition | 120 |
| 260 ppm NRB Composition | 160 |
| 300 ppm NRB Composition | 0 |

As is shown in Table 4, the NRB composition at 300 ppm was able to completely control H2S, outperforming the normal NRB program (480 ppm $Ca(NO_3)_2$) with 1 ppm live NRB culture) and performing at least as well as traditional Glut/Quat biocide. At 260 ppm and 240 ppm of the NRB composition resulted in a reduction in the amount of $H_2S$ produced compared to control, performing similarly to the normal NRB program.

Example 6

Example 6 was performed in accordance with Example 4 using mock produced water. Samples of the following were mixed with the mock produced water.
Control: No biocide or nitrate.
250 ppm 12.3 Glut/Quat Biocide: a mixture of glutaraldehyde and a quarternary ammonia compound was prepared
NRB Program: (480 ppm Ca(NO3)2 with 1 ppm live NRB culture.
100, 200 and 250 ppm NRB composition with 20 ppm $MoO_4$—NRB concentration at 30% active nitrate and 30% NRB culture.
20 ppm $MoO_4$
Table 5 shows the results.

TABLE 5

| Treatment | Total H2S (ppm) |
| --- | --- |
| Control | 2805 |
| 250 ppm 12:3 Glut/Quat Biocide | 6 |
| NRB Program (480 ppm CaNO3) | 25 |
| 20 ppm MoO4/100 ppm NRB Composition | 844 |
| 20 ppm MoO4/200 ppm NRB Composition | 657 |
| 20 ppm MoO4/250 ppm NRB Composition | 0 |
| 20 ppm MoO4 | 1974 |

In mock produced water, 250 ppm of the NRB composition combined with 20 ppm of molybdate performed substantially better than 20 ppm of molybdate alone, reducing the amount of $H_2S$ produced by about 70%. Combining 250 ppm of the NRB composition with 20 ppm of molybdate resulted in a level of $H_2S$ control comparable to that of traditional Glut/Quat biocide and NRB treatment (480 ppm $Ca(NO_3)_2$ with 1 ppm live NRB culture). The combination of molybdate and NRB composition required a lower concentration of both molybdate and NRB composition to achieve parity with currently used treatment methods.

Example 7

Example 7 was performed in accordance with Example 6 using actual produced water. Samples of the following were mixed with the mock produced water.
Control: No biocide or nitrate.
250 ppm 12.3 Glut/Quat Biocide: a mixture of glutaraldehyde and a quarternary ammonia compound was prepared
NRB Program: (480 ppm $Ca(NO_3)_2$ with 1 ppm live NRB culture.
250 ppm NRB composition with 20 ppm $MoO_4$—NRB concentration at 30% active nitrate and 30% NRB culture.
20 ppm MoO4.
Table 6 shows the results.

TABLE 6

| Treatment | Total H2S (ppm) |
| --- | --- |
| Control 1 | 6190 |
| 250 ppm 12:3 Glut/Quat Biocide | 7 |
| NRB Program (480 ppm CaNO3) | 83 |
| 250 ppm NRB Composition | 162 |
| 20 ppm MoO4/250 ppm NRB Composition | 0 |
| 20 ppm MoO4 | 3188 |

In actual produced water, proprietary blend: 30% live NRB culture, 30% active NO3) combined with 20 ppm of molybdate performed comparably to traditional Glut/Quat biocide treatment and outperformed NRB treatment (480 ppm $Ca(NO_3)_2$ with 1 ppm live NRB culture). This combination of the NRB composition and molybdate outperformed both components by themselves indicating a synergistic effect on H2S control.

Depending on the context, all references herein to the "disclosure" may in some cases refer to certain specific embodiments only. In other cases it may refer to subject matter recited in one or more, but not necessarily all, of the claims. While the foregoing is directed to embodiments, versions and examples of the present disclosure, which are included to enable a person of ordinary skill in the art to make and use the disclosures when the information in this patent is combined with available information and technology, the disclosures are not limited to only these particular embodiments, versions and examples. Other and further embodiments, versions and examples of the disclosure may be devised without departing from the basic scope thereof and the scope thereof is determined by the claims that follow.

What is claimed is:

1. A process comprising:
   growing nitrate reducing bacteria (NRB) in a nitrate reducing bacteria media to form a NRB culture, wherein the NRB is *Campylobacter* sp. *Nitrobacter* sp., *Thiobacillus* sp., *Nitrosomonas* sp., *Thiomicrospira* sp., *Sulfurospirillum* sp., *Thauera* sp., *Paracoccus* sp., *Pseudomonas* sp., or *Rhodobacter* sp;
   combining the NRB culture with a concentrated nitrate solution to form a NRB composition wherein the concentration of nitrate in the NRB composition is between 0.5% and 50% active nitrate (w/v); and
   injecting the NRB composition into a hydrocarbon-bearing formation.

2. The process of claim 1, wherein the formation further comprises a fracturing fluid or produced water.

3. The process of claim 2 further comprising injecting a molybdate or molybdate salt into the formation.

4. The process of claim 3, wherein the concentration of nitrate in the NRB composition is about 30% active nitrate (w/v).

5. The process of claim 4, wherein the only nitrate present in the NRB composition is sodium nitrate.

6. The process of claim 3, wherein the nitrate is sodium nitrate, potassium nitrate, or calcium nitrate.

7. The process of claim 1, wherein the NRB composition has a shelf life of at least 30 days.

8. The process of claim 1, wherein the step of forming an NRB composition further comprises:
   adding molybdate or a molybdate salt to the NRB composition.

9. A process comprising:
   growing nitrate reducing bacteria (NRB) in a nitrate reducing bacteria media to form a NRB culture, wherein the NRB is *Campylobacter* sp. *Nitrobacter* sp., *Thiobacillus* sp., *Nitrosomonas* sp., *Thiomicrospira* sp., *Sulfurospirillum* sp., *Thauera* sp., *Paracoccus* sp., *Pseudomonas* sp., or *Rhodobacter* sp;
   combining the NRB culture with molybdate or molybdate salt to form a NRB composition wherein the molybdate or molybdate salt is present in the NRB composition in an amount of between 3% and 15% (by weight of fluid); and
   injecting the NRB composition into a hydrocarbon-bearing formation.

10. The process of claim 9 further comprising:
    combining the NRB composition with a concentrated nitrate solution.

* * * * *